United States Patent [19]

Allemand

[11] Patent Number: 5,317,380
[45] Date of Patent: May 31, 1994

[54] PARTICLE DETECTION METHOD AND APPARATUS

[75] Inventor: Charly D. Allemand, Nantucket, Mass.

[73] Assignee: Inspex, Inc., Billerica, Mass.

[21] Appl. No.: 815,145

[22] Filed: Dec. 31, 1991

Related U.S. Application Data

[63] Continuation-in-part of Ser. No. 657,207, Feb. 19, 1991, abandoned.

[51] Int. Cl.$^5$ .......................................... G01N 21/88
[52] U.S. Cl. .................................. 356/338; 356/237; 356/239; 356/431; 250/572
[58] Field of Search .................. 356/335–343, 356/237, 239, 429–431, 371, 445; 250/562, 572, 574, 571

[56] References Cited

U.S. PATENT DOCUMENTS

| | | |
|---|---|---|
| 2,947,212 | 8/1960 | Woods . |
| 3,782,836 | 1/1974 | Fey et al. . |
| 4,337,340 | 3/1983 | Green et al. . |
| 4,342,515 | 8/1982 | Akiba et al. . |
| 4,468,120 | 8/1984 | Tanimoto et al. ............... 356/237 |
| 4,669,875 | 6/1987 | Shiba et al. ...................... 356/237 |
| 4,772,126 | 9/1988 | Allemand et al. . |
| 4,812,664 | 3/1989 | Borden ............................. 250/572 |
| 4,889,998 | 12/1989 | Hayano et al. .................. 356/237 |
| 4,898,471 | 2/1990 | Stonestrom et al. . |
| 4,941,719 | 7/1990 | Hisada et al. .................... 359/205 |
| 4,966,457 | 10/1990 | Hayano et al. .................. 356/237 |
| 5,076,692 | 12/1991 | Neukermans et al. ........... 356/338 |

FOREIGN PATENT DOCUMENTS

| | | |
|---|---|---|
| 0398781 | 11/1990 | European Pat. Off. . |
| 61-162738 | 7/1986 | Japan . |

OTHER PUBLICATIONS

Patent Abstracts of Japan, vol. 11, No. 340 (Nov. 7, 1987).
IBM Technical Disclosure Bulletin, vol. 12, No. 10, pp. 1672–1673 (Mar. 1970).
IBM Technical Disclosure Bulletin, vol. 21, No. 6, pp. 2336–2337 (Nov. 1978).
IBM Technical Disclosure Bulletin, vol. 27, No. 12, pp. 6971–6973 (May 1985).
IBM Technical Disclosure Bulletin, vol. 27, No. 12, pp. 6999–7001 (May 1985).
P. Burggraaf, Auto Wafer Inspection: Tools For Your Process Problems, Semiconductor International, pp. 54–61 (Dec. 1988).

*Primary Examiner*—Richard A. Rosenberger
*Assistant Examiner*—Hoa Q. Pham
*Attorney, Agent, or Firm*—Kriegsman & Kriegsman

[57] ABSTRACT

A method and apparatus for detecting particles on a surface of an object, such as a virgin or patterned semiconductor wafer, ceramic tile, or the like. In one embodiment, an apparatus is provided in which a scanning beam of laser light is brought to focus as an arcuate scan line on a surface of the object at a grazing angle of incidence using an off-axis hypertelecentric mirror. A pair of light detectors are positioned at a meridional angle of about 30 degrees and at an azimuthal angle of about 4 degrees to measure forward scattered light from the surface. The object is then moved translationally so that the beam can scan another line of the surface. A light trap is provided to trap light that is reflected by the surface, and a series of masks are provided to mask light which is scattered by the hypertelecentric mirror and, in the case of patterned objects, light which is diffracted by the pattern imprinted on the object.

26 Claims, 11 Drawing Sheets

PARTICLE DETECTION METHOD AND APPARATUS

This application is a continuation-in-part of U.S. Ser. No. 07/657,207, filed Feb. 19, 1991 now abandoned.

BACKGROUND OF THE INVENTION

The present invention relates generally to a method and apparatus for detecting the presence of particles on the surface of an object and more particularly to a method and apparatus for detecting and measuring the number and sizes of contaminant particles on the surface of an object, such as a patterned or virgin semiconductor wafer or ceramic tile, using the principle of light scattering.

There are a variety of existing ways for detecting and measuring the number and sizes of particles on the surface of a semiconductor wafer for the purpose of rejecting those wafers which have on their surface one or more particles above certain sizes or an excessive number of particles. One of the more simple methods involves having a human operator inspect the wafer using a light field/dark field microscope. Using the eye, the operator actually counts the number of particles and also identifies the size of the particles, such as those between 1 to 20 microns, and then rejects those wafers which have particles of or above a certain size or which have an excessive number of particles. This method, however, is highly inaccurate and very expensive both in terms of wages for the human operator and in terms of the number of rejects both after the inspection and after production of the chips (when an erroneously passed wafer is found to have an electrical defect, e.g., short circuits, because of the presence of contaminant particles).

In P. Burggraaf, "Auto Wafer Inspection: Tools for Your Process Problems," *Semiconductor International*, pp. 54–61 (December 1988), there are disclosed several types of automatic-vision wafer inspection systems, i.e., systems which do not require a human inspector. One type of system described is the Surfscan TM 7000 manufactured by Tencor Instruments, Mountain View, Calif. This light scattering system uses a laser beam, focused by a telecentric lens, to scan a patterned semiconductor wafer at a shallow angle of incidence, the patterned semiconductor wafer being aligned so that the pattern streets run parallel to the direction of scanning. Side scattered light from the wafer is then detected by a single photomultiplier tube disposed to the side of the wafer in the plane of the scan line.

In U.S. Pat. No. 4,898,471, issued Feb. 6, 1990, and assigned to Tencor Instruments, a system for detecting particles and other defects on a patterned semiconductor wafer, photomask, or the like is disclosed. The system, which corresponds generally to the above-described Surfscan TM 7000, includes a light source for emitting a beam of light. A polarizing filter is used to polarize the beam of light in a direction substantially parallel to the surface of the patterned semiconductor wafer to be examined. The beam is enlarged in cross-sectional diameter by a beam expander placed along the path of the beam after the polarizing filter. The beam is then caused to scan by a deflection mirror. A telecentric lens brings the scanning beam to focus on the patterned wafer at a shallow angle of incidence, the beam striking the wafer surface substantially parallel to the pattern streets formed on the wafer. A light collection system for detecting side scattered light is positioned in the plane of the scan line. The light collection system, which includes a lens for focusing the side scattered light, a polarizing filter oriented in a direction substantially parallel to the surface of the patterned wafer, and a photomultiplier tube for detecting light incident thereon and transmitting electrical signals in response thereto, receives light scattered in a direction less than 15 degrees above the surface and at angle relative to the beam direction in a range from about 80 degrees to 100 degrees. A processor constructs templates from the electrical signal corresponding to individual patterns and compares the templates to identify particles.

In U.S. Pat. No. 4,772,126 to C. D. Allemand et al., there is disclosed a method and apparatus for detecting the presence of particles on the surface of an object such as the front side of a patterned semiconductor wafer. A vertically expanded, horizontally scanning, beam of light is directed onto an area on the surface of the object at a grazing angle of incidence. A video camera positioned above the surface detects light scattered from any particles which may be present on the surface, but not specularly reflected light. The surface is angularly prepositioned (rotated) relative to the incident light beam so that the diffracted light from the surface and the pattern of lines on the surface is at a minimum. The object is then moved translationally to expose another area to the incident light beam so that the entire surface of the object or selected portions thereof can be examined, one area at a time.

In U.S. Pat. No. 4,377,340 to G. P. Green et al., there is disclosed a method and apparatus for detecting and measuring the number and sizes of impurities on the surface of a material, such as a semiconductor wafer, wherein a beam of high intensity collimated light from a xenon arc lamp is directed onto the surface at normal incidence in the absence of any extraneous light, through a collimating mirror and a pin hole device and whereat the particles will scatter the light, and wherein the surface is viewed by a high light sensitive TV camera which is positioned off-axis to pick up scattered light but not specularly reflected light for display on a viewing screen.

In IBM Technical Disclosure Bulletin, Volume 12, No. 10, pp. 1672–1673, dated March, 1970, there is disclosed a system for detecting repeated geometric defects on a reflecting surface. The system comprises a light source combined with a collimator. A beam splitter splits the incident beam into a first beam, which is directed to the wafer, and a second beam, which is directed to a light absorbing surface. The wafer is mounted on a tilted rotatable support. An aperture plate limits the size of the light beam incident upon the sample and at the same time restricts the amount of light reflected back along the direction of the incident beam to a photomultiplier by the surface defects. The incident beam is split by the wafer, the planar surface of the wafer directing the major portion of the beam back to the back side of the aperture plate whereas the defects on the wafer direct a portion of the beam back through the aperture plate. The portion of the beam transmitted through the aperture plate strikes a beam splitter and is directed through a telescope to a photomultiplier.

In IBM Technical Disclosure Bulletin, Volume 21, No. 6, pp. 2336–2337, dated November, 1978, there is disclosed a system for detecting defects on wafers wherein light from a plurality of ring light sources impinges on the wafer at an oblique angle to the wafer surface and wherein light scattered upward from the surface at right angle thereto is fed by a lens system into a broad band array detector.

In IBM Technical Disclosure Bulletin, Volume 27, No. 12, pp. 6971-6973, dated May, 1985, there is disclosed an inspection system for particulate and defect detection on product wafers wherein light from an illuminator impinges on the substrate at an angle of 0 to 5 degrees. Additionally, the beam is oriented at a preferred angle, e.g., 45 degrees, with respect to the wafer circuit geometry. A photomultiplier tube is arranged above the substrate to monitor light scattered therefrom.

In IBM Technical Disclosure Bulletin, Volume 27, No. 12, pp. 6999-7001, dated May, 1985, there is disclosed an automated, grazing angle, oblique light, inspection system for the detection of particulate contamination and metallization defects on semiconductor product wafers.

In U.S. Pat. No. 2,947,212 to R. C. Woods, there is disclosed a method of detecting surface conditions on a strip of sheet metal having line markings in which light from a light source is directed towards the surface of the sheet metal in a direction generally perpendicular to the line markings. Non-specular reflection in a selected direction which is perpendicular to the lines, and which is preferably between the angle of incidence and the angle of specular reflection, is monitored by a photoelectric cell which is able to detect a surface flaw by variation in the intensity of the reflected light. The light in the incident beam may be polarized and the light in the selected non-specular reflected beam filtered to pass only such polarized light.

In U.S. Pat. No. 4,342,515 to M. Akiba et al., there is disclosed an inspection apparatus for detecting unfavorable foreign matters existent on the surface of an object such as a semiconductor wafer. The apparatus includes a collimated beam generator portion which projects a collimated beam towards the object to be inspected from a side thereof and a mechanism which senses light reflected from the surface of the object, through a polarizer plate. In accordance with the disclosed technique for using the apparatus, the signal-to-noise ratio between a detection signal generated by a pattern of the foreign matter to be detected and a signal generated by a normal pattern of the object surface and sensed as a noise component are said to be enhanced.

In U.S. Pat. No. 3,782,836 to C. F. Fey et al., there is disclosed a surface irregularity analyzing system which includes structure for directing light towards a surface in a direction having a certain angular relationship to the surface. If the light strikes irregularities in the surface it is reflected in a direction having an angular relationship to the surface other than equal and opposite the incident direction. The amount of light reflected from irregularities in the surface is determined, either photographically or photoelectrically using a detector positioned over the surface, to provide an analysis of irregularities in the surface.

In Japanese Patent No. 61-162738 assigned to Hitachi, Ltd., there is disclosed a method for preventing a circuit pattern from being misjudged to a foreign matter, the method employing a flat spot-shaped scan laser beam.

SUMMARY OF THE INVENTION

It is an object of the present invention to provide a new and improved method and apparatus for detecting the presence of contaminant particles on a surface of an object using the principle of scattered light.

It is another object of the present invention to provide a method and apparatus as described above which can be used to detect the presence of contaminant particles on both virgin and patterned semiconductor wafers, ceramic tiles, and the like.

It is yet another object of the present invention to provide a method and apparatus as described above in which the signal to background ratio and the signal to noise ratio are optimized.

It is still another object of the present invention to provide a method and apparatus as described above which is capable of detecting contaminant particles as small as about 0.8 microns on patterned tiles.

It is a further object of the present invention to provide a method and apparatus as described above which is designed especially for use in dark field illumination applications.

Other objects, as well as features and advantages of the present invention, will be set forth in part in the description which follows, and in part will be obvious from the description or may be learned by practice of the invention. The objects, features, and advantages of the invention may be realized and attained by means of the instrumentalities and combinations particularly pointed out in the appended claims.

In accordance with the teachings of the present invention, a method for detecting particles on a surface of an object comprises the steps of (a) providing a beam of light; (b) bringing said beam to focus on the surface at a grazing angle of incidence; and (c) detecting forward scattered light from the surface.

Also in accordance with the teachings of the present invention, an apparatus for detecting particles on the surface of an object comprises (a) means for providing a beam of light; (b) means for bringing said beam to focus on the surface at a grazing angle of incidence; and (c) means for detecting forward scattered light from the surface.

As used throughout the present specification and claims, the term "forward scattered light" is to be contrasted with the terms "back scattered light" and "side scattered light" and is not intended to encompass, as is the case with U.S. Pat. No. 4,898,471, forwardly-directed scattered light of the type that would ordinarily be collected by typical focusing optics positioned along the plane of a scan line to receive side scattered light.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings wherein like reference numerals represent like parts.

DETAILED DESCRIPTION OF PREFERRED EMBODIMENTS

The present invention is directed to a method and apparatus for detecting contaminant particles present on the surface of an object. The invention is based, in part, on the discovery that improved signal to background and signal to noise ratios may be obtained by bringing a beam of light to focus on the surface of the object at a grazing angle and measuring forward scattered light from the surface. Preferably, the forward scattered light is observed at a meridional angle of about 5 to 60 degrees, more preferably at about 30 degrees, and at an azimuthal angle of about 2 to about 10 degrees, more preferably at about 4 degrees. For purposes of the present specification and claims, "meridional angle" is the angle between the plane of incidence of the illumination beam and the observation beam, and "azimuthal angle" is the angle between the observation beam and the surface being inspected.

Figure 1:
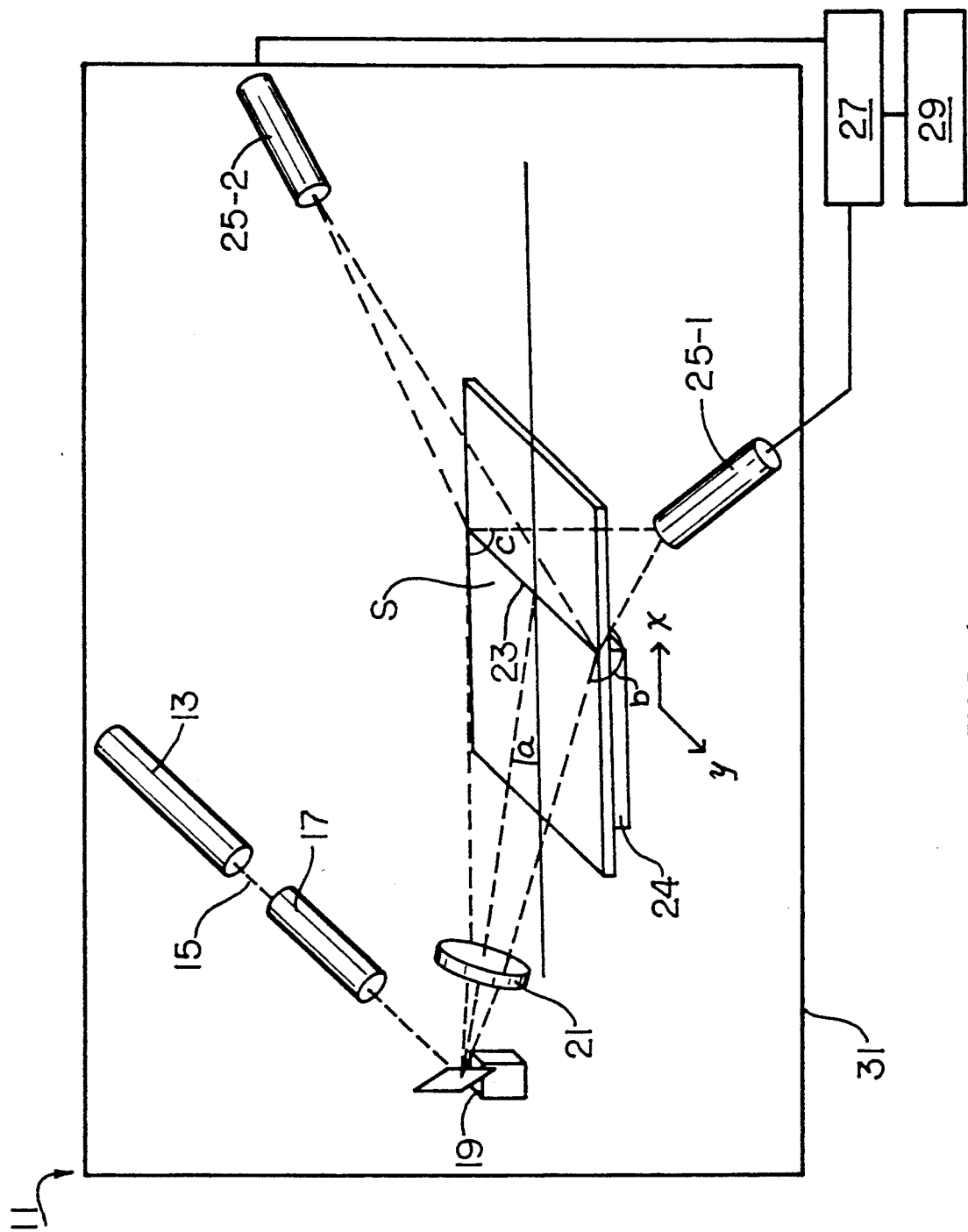
FIG. 1 is a schematic representation of one embodiment of an apparatus for detecting particles on the surface of an object, the apparatus being constructed according to the teachings of the present invention.
Figure 2:
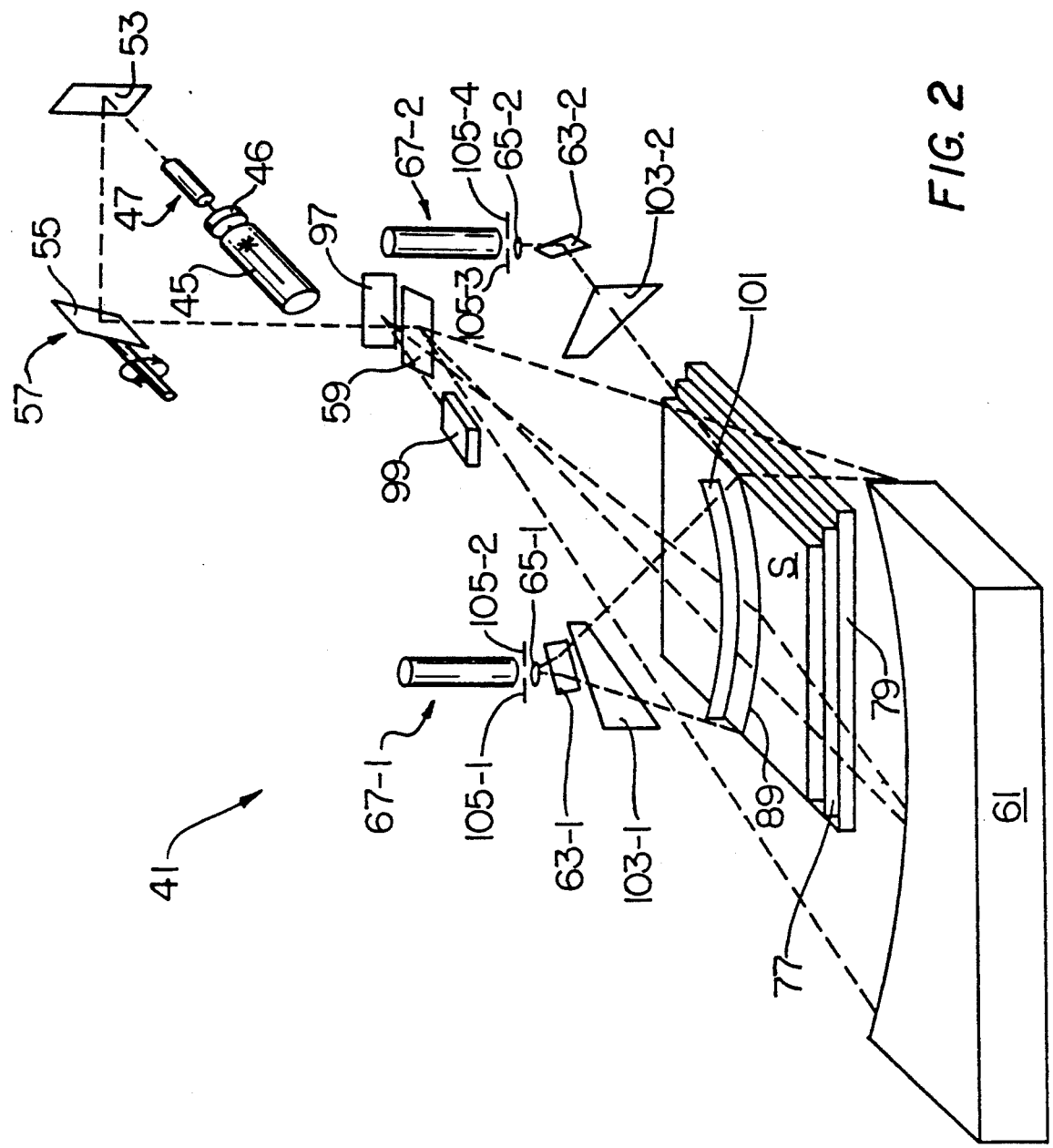
FIG. 2 is a pictorial representation of a second embodiment of an apparatus constructed according to the teachings of the present invention for detecting particles on the surface of an object, the housing and optical plate not being shown.

Referring now to FIG. 1, there is illustrated an apparatus for detecting particles on a surface of an object, the apparatus being constructed according to the teachings of the present invention and represented generally by reference numeral 11.

Apparatus 11 includes a laser 13 for outputting a beam of laser light 15. Preferably, laser 13 is a 40 mW Nd:YAG laser which produces monochromatic light at 532 nm. Beam 15 is first expanded in cross-section and caused to converge by an expander 17 and is then deflected by a galvanometer 19 which causes the beam to scan in the y-direction, preferably at a rate of about 50/sec. The beam then passes through an $F\theta$ lens 21 which brings the beam to focus as a small spot or point on a straight scan line 23 on a specimen S, such as a semiconductor wafer or a tile, at a grazing angle a. Grazing angle a is preferably an angle of between about 80 degrees and 90 degrees from the normal to the specimen surface (i.e., between 0 and about 10 degrees from the plane of the specimen surface), more preferably an angle of about 80 degrees from the normal to the specimen surface.

The specimen is mounted on a holder (i.e. stage) 24 which is in the form of a vacuum chuck. Holder 24 is mounted such that it can be moved in the x-direction so that the entire surface of the specimen can be illuminated, a scan line at a time. Preferably, holder 24 moves at such a speed that the entire surface of the specimen can be illuminated in about 20 seconds.

The light scattered from the specimen is detected by a pair of photomultiplier tubes 25-1 and 25-2, which are preferably disposed at a meridional angle of about 30 degrees and at an azimuthal angle of about 4 degrees. The electrical signals outputted by photomultiplier tubes 25 are then fed into a computer 27 for processing and displayed on a display 29.

The entire apparatus 11, except for computer 27 and display 29, is enclosed within a light tight housing 31 so that extraneous light is not mistakenly detected. Preferably, the inner walls of housing 31 are coated with a dark, non-reflective surface.

As can be appreciated, the meridional angle between the incident beam and the observation beam is not constant over the entire length of the scan line. This is best visualized by referring to FIG. 1 and noting the difference in angles b and c. As discussed above, because certain meridional angles, such as the 30 degree angle, have been found to optimize the signal to background and signal to noise ratios, it is clear that keeping the meridional angle constant over the length of the scan line is highly desirable.

Referring now to FIGS. 2-8 and in particular to FIGS. 2-5, there is illustrated another embodiment of an apparatus for detecting particles on a surface of an object, such as a virgin or patterned semiconductor wafer, ceramic tile, or the like, the apparatus being constructed according to the teachings of the present invention and represented generally by reference numeral 41.

For the reasons to be discussed below in greater detail, apparatus 41 solves the problem encountered by apparatus 11 of keeping the meridional angle of observation constant over the entire length of the scan line.

Apparatus 41 includes a housing 43 (not shown in FIG. 2) which is light tight and whose inner walls are coated with a dark, non-reflective material. Preferably, the dimensions of housing 43 are 24 inches in length, 18 inches in width, and 20.5 inches in depth. An optical plate 44 (not shown in FIG. 2), which is also coated with a dark, non-reflective surface, is mounted within housing 41 to support some of the optical components to be discussed below.

A laser 45, which produces an intense beam of collimated light, is disposed within housing 43 on plate 44. Preferably, laser 45 is a 40 mW Nd:YAG laser with an output at 532 nm. The beam generated by laser 45 is passed through a variable neutral density filter 46, which may attenuate the beam, and an expander 47, whose first lens 49 enlarges the cross-sectional diameter of the beam by a magnitude of about 10 and whose second lens 51 causes the beam to converge. (Second lens 51 need not be a converging lens; however, by so being, a smaller concave mirror of the type to be discussed below may be used and/or the distance between the concave mirror and the scan line may be reduced.)

Figure 5:
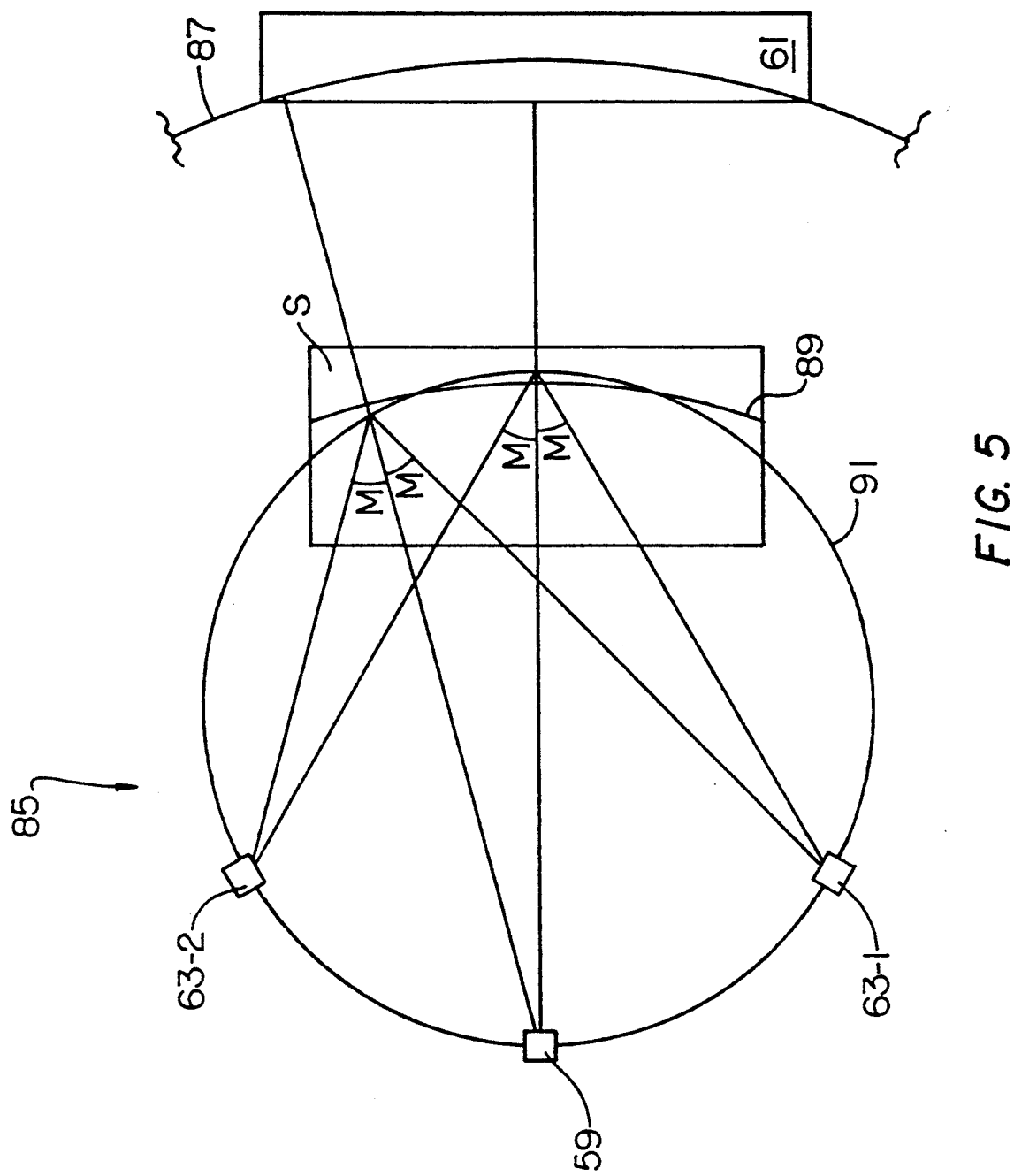
FIG. 5 is a schematic plan view of the portion of the apparatus shown in FIG. 3 represented by reference numeral 85.
Figure 5A:
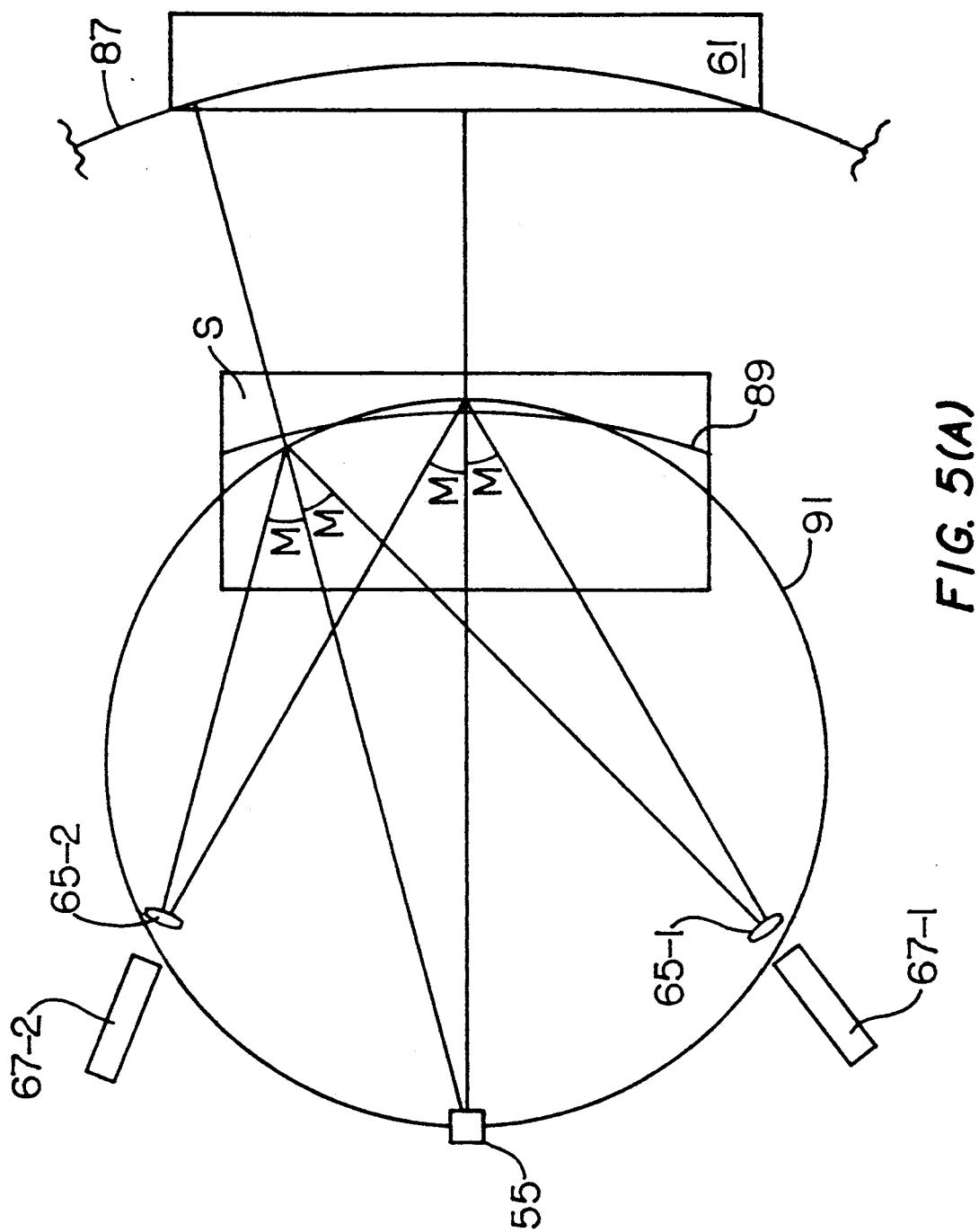
FIG. 5(a) is a schematic plan view of a portion of an apparatus corresponding to FIG. 5 in which mirrors 59, 63-1, and 63-2 have been removed.
Figure 6:
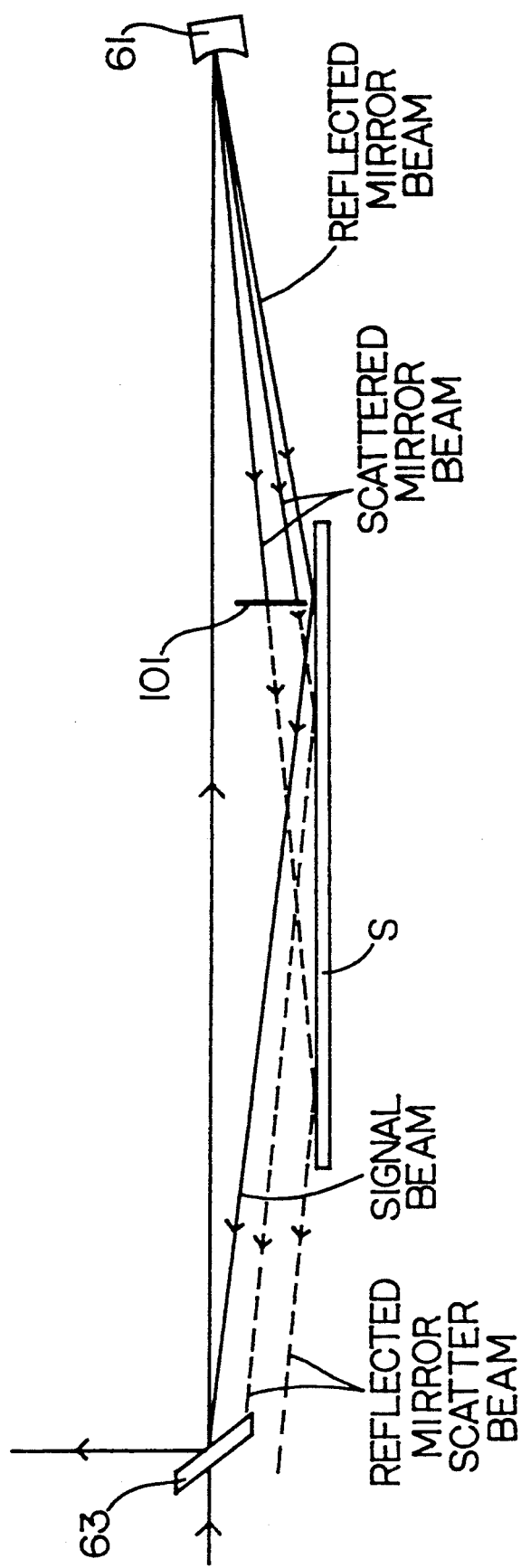
FIG. 6 is a schematic front view of a portion of the apparatus shown in FIG. 2, illustrating the placement of the scan line mask.
Figure 7:
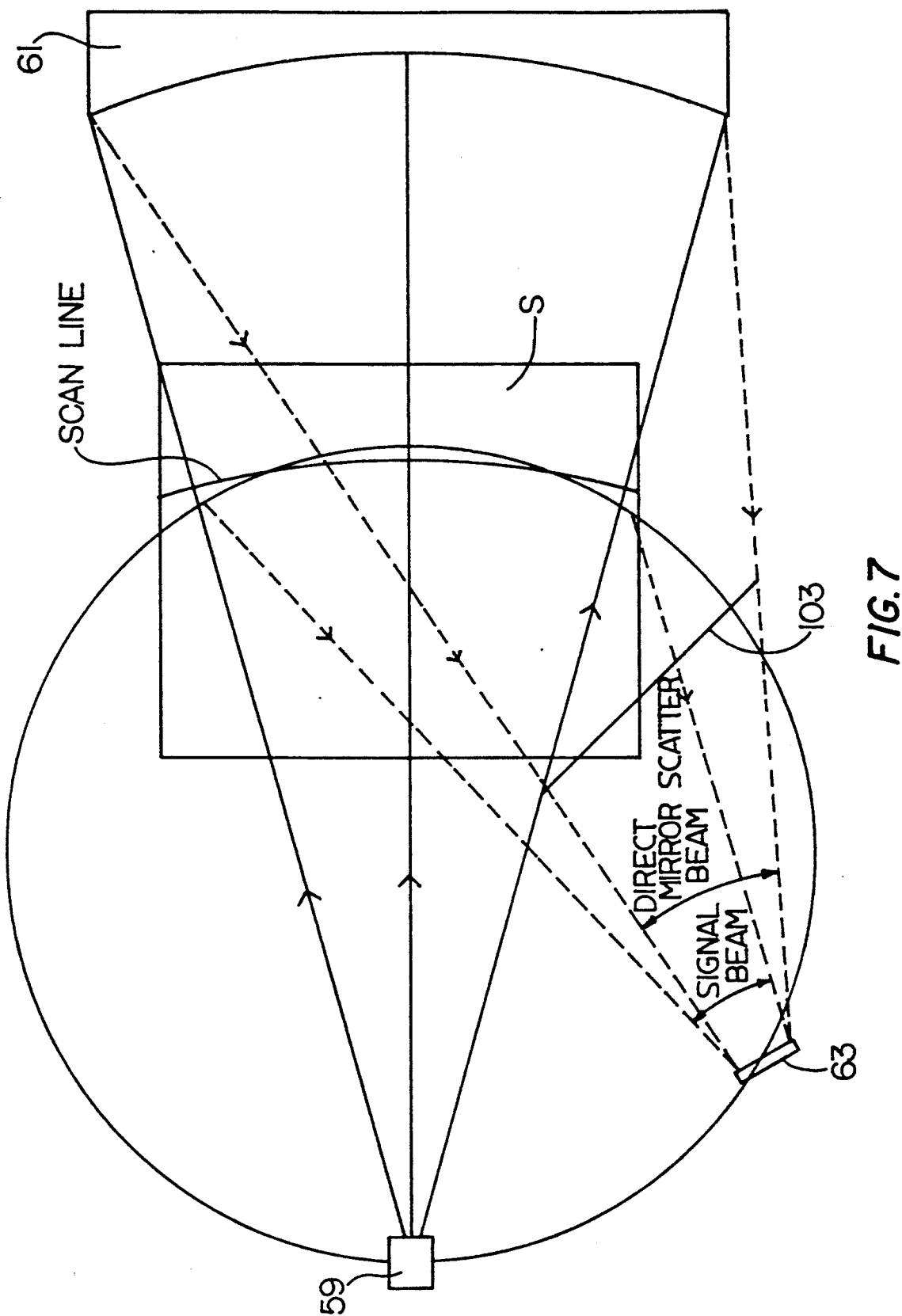
FIG. 7 is a schematic front view of a portion of the apparatus shown in FIG. 2, illustrating the placement of the mirror scatter mask.
Figure 8:
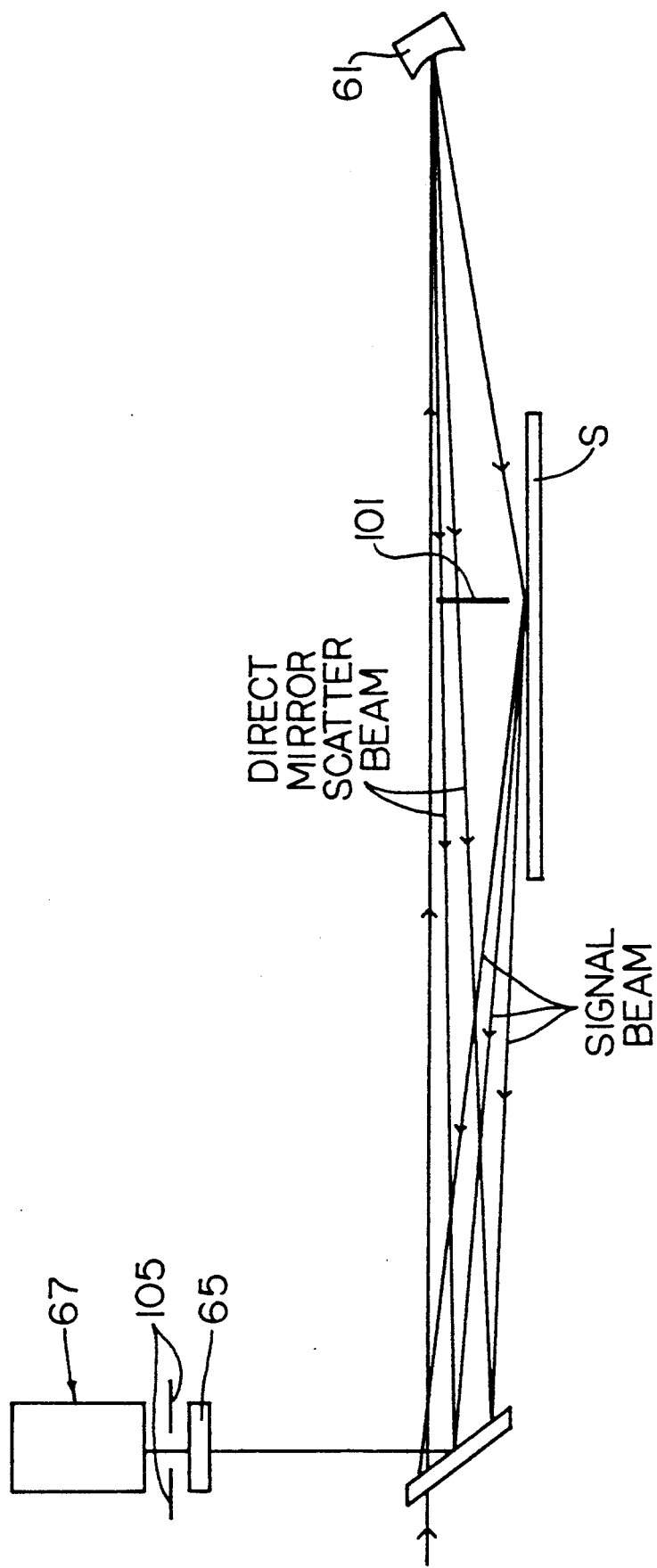
FIG. 8 is a schematic top view of a portion of the apparatus shown in FIG. 2, illustrating the placement of the focal mask.

After emerging from expander 47, the beam is deflected off a 45 degree mirror 53, which directs the beam to a scanning mirror 55 of a galvanometer 57. Preferably, galvanometer 57 is set so that mirror 55 scans approximately 50 times per second. Scanning mirror 55 deflects the beam downwardly through a hole in optical plate 44 where it is deflected off a 45 degree mirror 59 disposed at the center of a circle defined by an off-axis hypertelecentric mirror 61. (It is to be understood that the purpose of mirror 59 is merely to alter the direction of the scanning beam so as to permit apparatus 41 to be reduced in size and that mirror 59 could be eliminated, as seen in FIG. 5(a), by placing mirror 55 of galvanometer 57 where mirror 59 is shown in FIG. 5.)

Hypertelecentric mirror 61, which is angled downwardly about 5 degrees, brings the beam deflected by mirror 59 to focus as a curved scan line 89 on a specimen S at a grazing angle of preferably between about 80 and 90 degrees from the normal to the specimen, more preferably at about 80 degrees from the normal to the specimen.

Where, for example, mirror 59 is disposed at the center of a 1110 mm diameter circle 87 (partially shown in FIG. 5) defined by mirror 61, the light beam comes to focus on the specimen S as an arcuate scan line 89 having a length of about 200 mm and whose midpoint is about 375 mm from mirror 59.

If specimen S is a patterned object, optimum results are obtained if the light beam strikes the specimen surface at an angle which is not parallel to the direction of the streets of the pattern, but rather, as set forth in U.S. Pat. No. 4,772,126, which issued Sep. 20, 1988 with inventors C. D. Allemand et al., at about a 45 degree angle relative to the pattern streets.

The light scattered from the specimen S is deflected by a pair of symmetrically disposed mirrors 63-1 and 63-2, which direct the scattered light to respective sets of lenses 65-1 and 65-2 and detectors 67-1 and 67-2. (It is to be understood that mirrors 63-1 and 63-2 are used merely to reduce the size of the apparatus and that they could be eliminated, as seen in FIG. 5(a), by positioning lenses 65 and/or detectors 67 where mirrors 63 are currently shown in FIG. 5.) For purposes of keeping the meridional angle of observation constant over the scan line, as will be discussed below in greater detail, mirrors 63-1 and 63-2, mirror 59, and arcuate scan line 89 are positioned so that when viewed from directly above they appear to lie along the circumference of an imaginary circle 91. Mirrors 63 are disposed at a meridional angle of preferably 5-60 degrees, more preferably 30 degrees, and at an azimuthal angle of preferably 2-10 degrees, more preferably 4 degrees.

As noted above, the light deflected by mirrors 63-1 and 63-2 passes through respective holes in optical plate 44 and is focused by lenses 65-1 and 65-2, which are preferably 30 mm bi-convex lenses, onto a pair of detectors 67-1 and 67-2. One advantage to using a pair of symmetrically disposed detectors, instead of a single detector, to measure the scattered light is that one can maintain an optimum signal to noise ratio as the illumination beam moves across the scan line. As can readily be appreciated, the intensity of the detected light signal varies as a function of the distance between the detector and that point of the scan line being illuminated. When using only one detector, the variation in the intensity of the light signal as a function of distance can be corrected using computer software; however, because the amount of noise calculated by the computer will itself be dependent upon the signal detected, an optimum signal to noise ratio will not be attained. By way of contrast, if one uses two symmetrically placed detectors, the intensity of the signal will be more constant over the entire scan line, permitting a better signal to noise ratio to be achieved.

Each detector 67 includes an optical fiber 69, onto which the light focused by lens 65 is imaged, and a photomultiplier tube 71, which is optically coupled to the output of fiber 69. Preferably, the output of fiber 69 and the input of tube 71 are brought into contact with a contact gel (not shown). The reason for using optical fiber 69 rather than imaging the scan line directly onto tube 71 is that the photocathode of tube 71 does not have a uniform response across its surface. Consequently, when the scan line is imaged onto the photocathode, the signal shows up stronger at the center of the photocathode and weaker radially outward. To correct for this lack of uniformity, the scan line is imaged by lens 65 onto fiber 69 which converges it to a small circle (e.g., 8-10 mm) on photomultiplier tube 71.

The outputs from tubes 71 are processed by a computer 73, which adds the signals using a fixed circuit or which adjusts each signal to account for the possibly different distances from the point of scattering to the respective detectors and then adds the signals. Instead of an addition, and "and" gate could be used for the following reason: Because two photomultiplier tubes are used, the maximum background signal may not appear at the same time for each photomultiplier tube whereas the maximum particle signal appears simultaneously on both tubes. After processing by the computer, the results are transmitted to a display 75.

The specimen is mounted on a holder 77, which is preferably a vacuum chuck. Holder 77 is mounted on a stage 79, which is preferably a telescoping stage to facilitate the mounting and removal of the substrate from holder 77. Holder 77 is mechanically coupled through a shaft to a motor 81 which causes holder 77 to slide on top of stage 79 in the direction of mirror 61. In this way, over a period of about 20 seconds, the entire surface of the specimen can be illuminated, one scan line at a time. If desired, motor 81 may be coupled to computer 73 so that the speed at which holder 77 slides towards mirror 61 may be adjusted.

Figure 3:
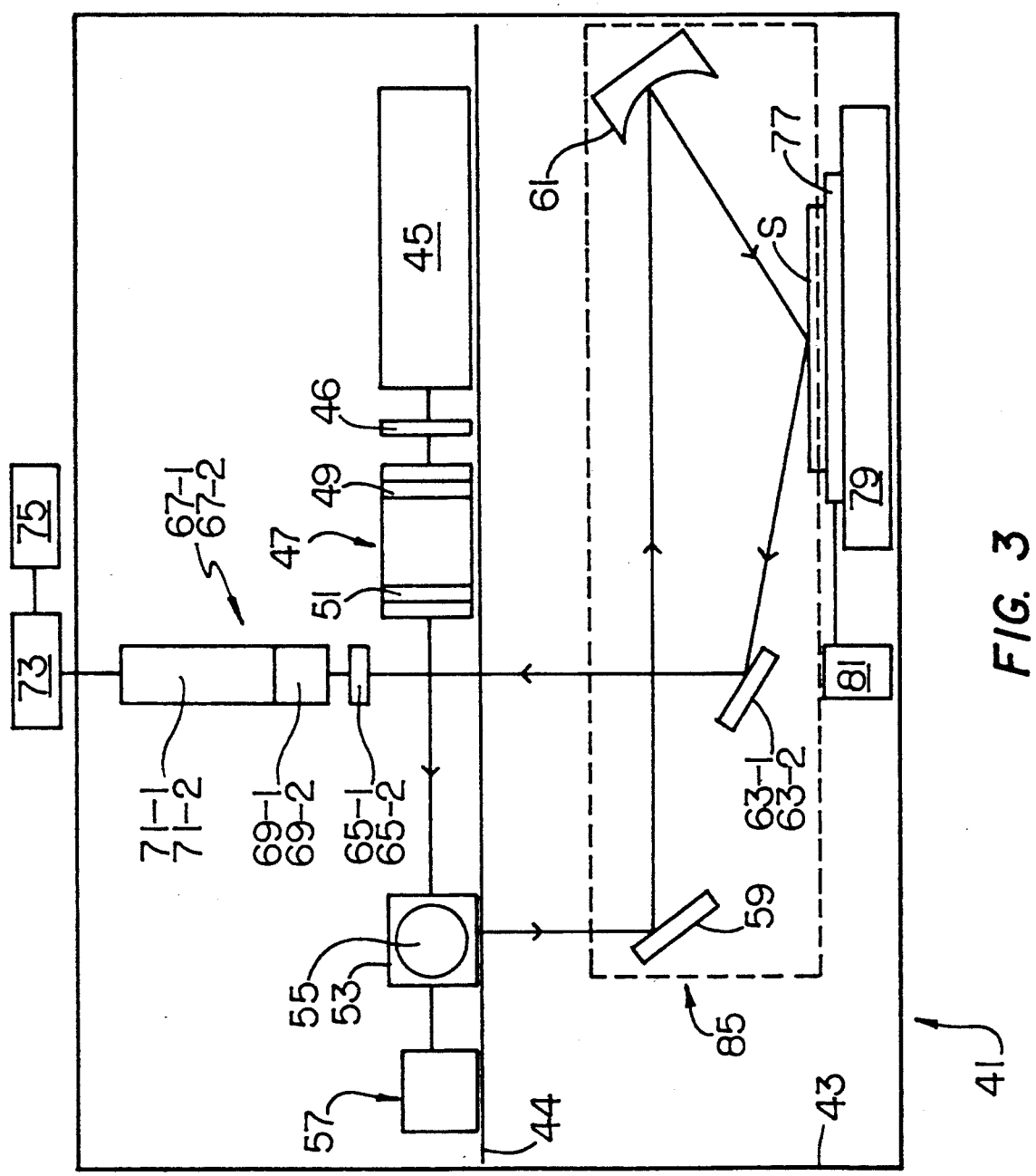
FIG. 3 is a schematic side view of the apparatus shown in FIG. 2, the masking and trapping components not being shown.
Figure 4:
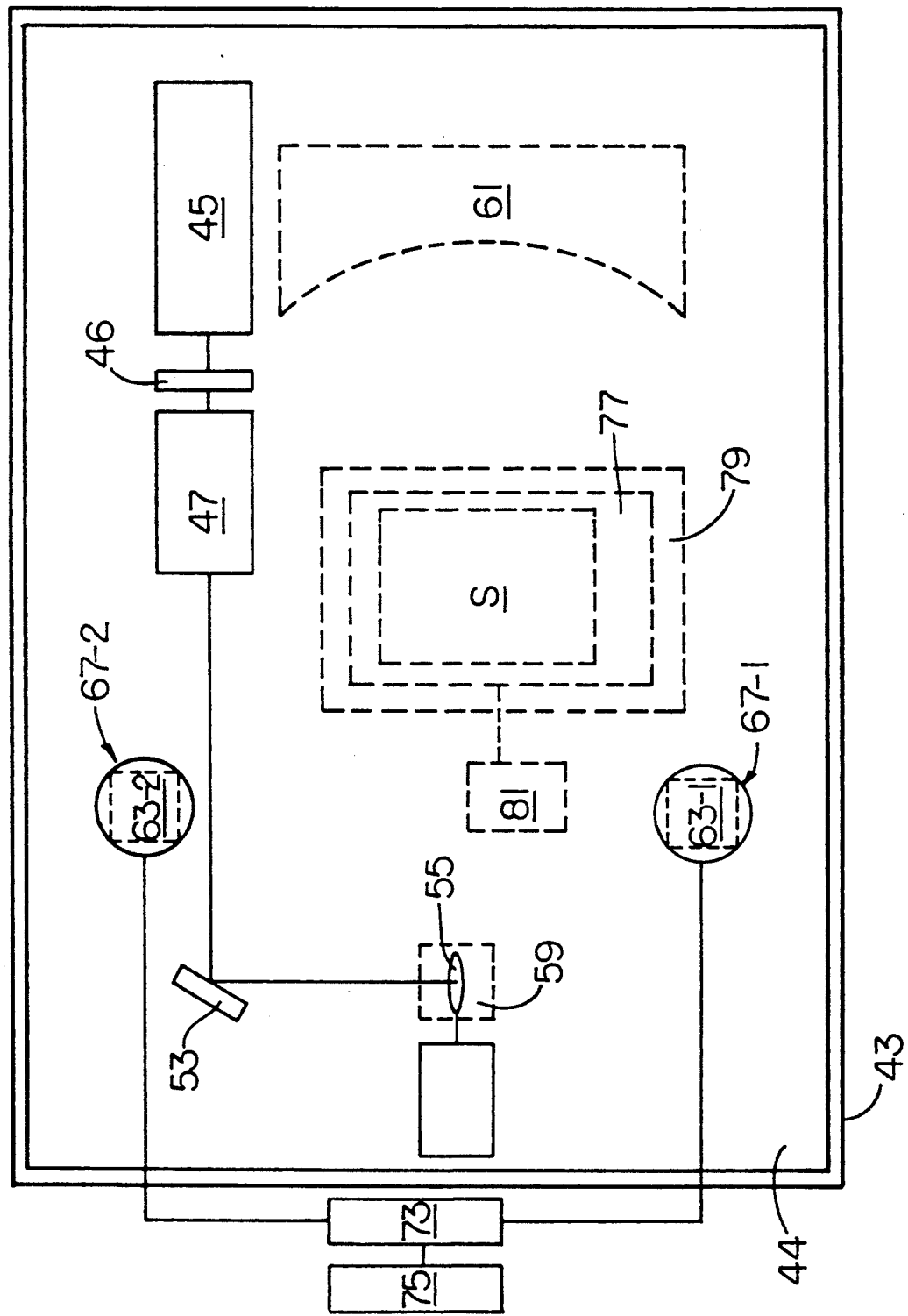
FIG. 4 is a schematic top view of the apparatus shown in FIG. 2, the masking and trapping components of the apparatus not being shown and the components disposed below the optical plate being represented by dashed lines.

Referring now in particular to FIG. 5, a plan view of that portion of apparatus 41 that is represented by reference numeral 85 in FIG. 3 is shown in order to illustrate how the geometric configuration of apparatus 41 solves the problem discussed above in connection with apparatus 11, namely, the problem of keeping the meridional angle of observation constant along the entire scan line. As seen by FIG. 5, when mirror 59, mirrors 63-1 and 63-2, and scan line 89 are viewed from directly above, they appear to be situated on the circumference of an imaginary circle 91. (It is to be understood that one or more of mirror 59, mirrors 63, and scan line 89 may be located on different planes and that while mirror 59 and mirrors 63-1 and 63-2 are shown in FIG. 5 and referred to herein, mirrors 59 and 63 could be replaced with galvanometer 57 and/or lenses 65-1 and 65-2, respectively.) Because mirror 59, mirrors 63, and scan line 89 are thus situated, the meridional angle of observation m for each detector will be the same at every point along the length of the scan line. Moreover, because mirrors 63 are symmetrically disposed, preferably at about a 30 degree angle relative to mirror 59, the meridional angle of observation m will be the same for both detectors.

Where, for example, the diameter of circle 87 is 1110 mm and the midpoint of scan line 89 is about 375 mm from mirror 61, the diameter of circle 91 will be approximately 382 mm.

Referring back now to FIG. 2, there can be seen the trapping and masking components of apparatus 41. The trapping components are used to trap the light that is reflected off, rather than scattered by, the specimen. If the reflected light is not trapped, it might otherwise find its way to the detectors and be picked up as background. In the embodiment shown, the trapping components include a trapping mirror 97 and a trap 99. Trapping mirror 97, which deflects the reflected beam into trap 99, is preferably placed along the path of the reflected beam at the point where it converges to a point, i.e., at approximately the center of the circle defined by mirror 61. Trap 99 may be a conventional light trap consisting of a multi-walled enclosure which is coated with a dark, non-reflective material.

The masking components for apparatus 41 are used to minimize the amount of light picked up by the detectors as a result of scattering of the beam by mirror 61. In the embodiment shown, the masking components include a scan line mask 101, a pair of mirror scatter masks 103-1 and 103-2, and four focal masks 105-1 through 105-4. Scan line mask 101 is a curved, dark, non-reflective wall disposed a short distance over the scan line. Mask 101 masks the light scattered by mirror 61 which, if left unmasked, would strike the substrate and possibly be reflected off mirror 63 (see FIG. 6). Mirror scatter masks 103-1 and 103-2, which are flat, dark, non-reflective walls, extend backwards and inwards from either side of mask 101. Masks 103-1 and 103-2 mask the light which is scattered by mirror 61 directly onto mirror 63 (see FIG. 7). Masks 103-1 and 103-2, however, do not extend so far downwardly that the signal beam becomes masked. Focal masks 105, a pair of which are disposed between each lens 65 and detector 67 on the image plane of lens 65, also mask the light which is scattered by mirror 61 directly onto mirror 63 (see FIG. 8).

While apparatus 41 may be used to detect particles on the surfaces of both virgin and patterned semiconductor wafers, ceramic tiles, and the like, it has been found that illumination of the pattern on patterned objects causes diffraction of the light beam, which may then be detected by detectors 67-1 and 67-2, thereby creating the possibility that an erroneous indication of the presence of a particle may occur.

Figure 9:
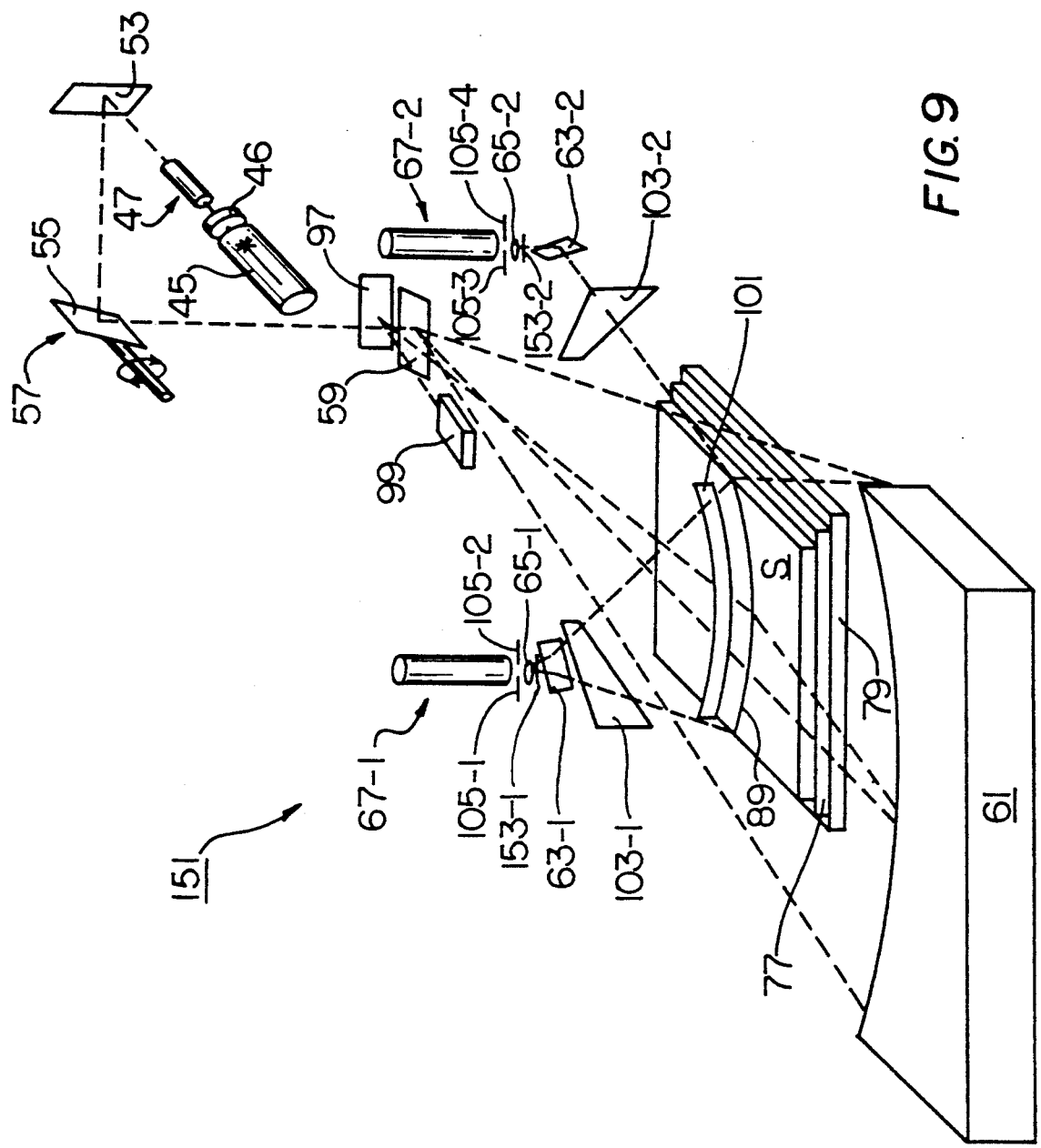
FIG. 9 is a pictorial representation of an embodiment of an apparatus constructed according to the teachings of the present invention for detecting particles on the surface of a patterned semiconductor wafer, ceramic tile or the like, the housing and optical plate not being shown.

Referring now to FIG. 9, there is shown an embodiment of an apparatus constructed according to the teachings of the present invention for detecting particles on the surface of a patterned object, such as a semiconductor wafer, ceramic tile, or the like, the apparatus being represented generally by reference numeral 151.

Figure 10:
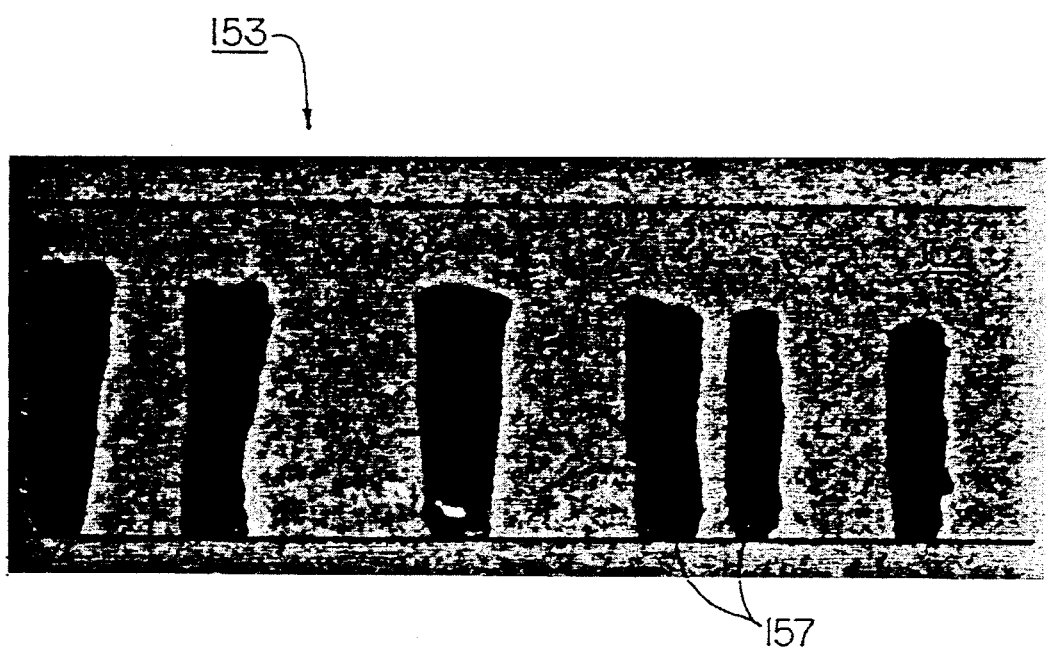
FIG. 10 is a top plan view of one of the diffraction masks shown in FIG. 9.

Apparatus 151 is similar in construction and operation to apparatus 41, the only difference between the two being that apparatus 151 additionally includes a pair of identical masks 153-1 and 153-2, mask 153-1 being disposed between mirror 63-1 and lens 65-1 and mask 153-2 being disposed between mirror 63-2 and lens 65-2. As seen in FIG. 10, each mask 153 preferably comprises a transparent substrate 155, such as a glass slide or the like, onto which are marked one or more non-transparent bands 157, which correspond to the diffraction pattern created by illumination of the patterned specimen S being examined. As can readily be appreciated, the specific arrangement of bands 157 on substrate 155 will depend upon the particular configuration of the pattern imprinted on the specimen. If the specimen has a narrow pattern imprinted thereon, light will be diffracted at wide angles, and the number of bands 157 will be comparatively small. In contrast, if the specimen has a wide pattern imprinted thereon, light will be diffracted at narrow angles, and the number of bands 157 will be comparatively large.

In another embodiment (not shown), detectors 67-1 and 67-2 are replaced with a pair of optical fibers (or with a bifurcated optical fiber) which are optically coupled, preferably through a contact gel, to a single photomultiplier tube.

Other embodiments (not shown) include substituting an array of photodiodes for the photomultiplier tubes to avoid the "aging problem" associated with photomultiplier tubes, mounting a pellicle on the concave mirror to keep it clean, using a photomultiplier log amplifier to increase the dynamic range of the photomultiplier, using an L.E.D. lamp lowered to the height of the scan line to check on the long term stability of the direction, using a zener clamp on the dynode network to reduce saturation and recovery time, using a transportation stage wider than the length of the scan line in order to enable observation of wide samples with multiple passes, and using blue light from an argon laser to increase the particle signal.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for detecting particles on a surface of an object comprising the steps of:
   a) providing a scanning beam of light;
   b) bringing said scanning beam of light to focus as a scan line on the surface of the object at a grazing angle of incidence; and
   c) measuring forward scattered light from the surface of the object, said measuring comprising observing forward scattered light at a meridional angle of between about 5 degrees and about 60 degrees, said meridional angle being constant over said scan line.

2. The method as claimed in claim 1 further comprising repeating steps (b) and (c) for the remainder of the surface.

3. The method as claimed in claim 1 wherein said meridional angle is about 30 degrees.

4. The method as claimed in claim 3 wherein said measuring step also comprises observing forward scattered light at an azimuthal angle of about 4 degrees.

5. The method as claimed in claim 1 wherein said measuring step also comprises observing forward scattered light at an azimuthal angle of about 2 to about 10 degrees.

6. The method as claimed in claim 5 wherein said azimuthal angle is about 4 degrees.

7. The method as claimed in claim 1 wherein said grazing angle of incidence is an angle between about 80 degrees and 90 degrees from the normal to the surface of the object.

8. The method as claimed in claim 7 wherein said grazing angle of incidence is about 80 degrees from the normal to the surface of the object.

9. The method as claimed in claim 11 wherein the object is a virgin semiconductor wafer.

10. The method as claimed in claim 11 wherein the object is a virgin ceramic tile.

11. An apparatus for detecting particles on a surface of an object comprising:
   a) means for providing a scanning beam of light;
   b) means for bringing said scanning beam of light to focus as an arcuately-shaped scan line on the surface of the object at a grazing angle of incidence; and
   c) means for measuring forward scattered light from the surface of the object;
   d) wherein said arcuately-shaped scan line, said scanning means and said measuring means are all disposed so as to appear, when viewed from above, to lie substantially along the circumference of a circle, with said scanning means being situated equidistant from the ends of said arcuately-shaped scan line;
   e) whereby forward scattered light is observed by said measuring means at a constant meridional angle over substantially the entirely of said arcuately-shaped scan line.

12. The apparatus as claimed in claim 11 further comprising means for repeating steps (b) and (c) for the remainder of the surface of the object.

13. The apparatus as claimed in claim 11 wherein said focusing means comprises an off-axis hypertelecentric mirror disposed along the path of said scanning beam of light so as to cause said scan line on the surface of the object to be arcuately-shaped.

14. The apparatus as claimed in claim 13 wherein said off-axis hypertelecentric mirror is oriented relative to the surface of the object so that said grazing angle of incidence is about 80 degrees from the normal to the surface of the object.

15. The apparatus as claimed in claim 13 further comprising means for masking the light scattered by said off-axis hypertelecentric mirror.

16. The apparatus as claimed in claim 11 wherein said means for providing a scanning beam of light comprises a galvanometer.

17. The apparatus as claimed in claim 11 wherein said measuring means comprises a detector, said detector being placed at a meridional angle of about 5 to about 60 degrees and at an azimuthal angle of about 2 to about 10 degrees.

18. The apparatus as claimed in claim 17 wherein said detector is placed at a meridional angle of about 30 degrees and at an azimuthal angle of about 4 degrees.

19. The apparatus as claimed in claim 11 wherein said measuring means comprises a pair of detectors, said pair of detectors being symmetrically disposed on opposite sides of said scanning beam of light at a meridional angle of about 5 to about 60 degrees and at an azimuthal angle of about 2 to about 10 degrees.

20. The apparatus as claimed in claim 19 wherein said meridional angle is about 30 degrees and said azimuthal angle is about 4 degrees.

21. The apparatus as claimed in claim 19 further comprising computer means coupled to said pair of detectors for storing and/or processing information from said pair of detectors and a display coupled to said computer for displaying the stored and/or processed information.

22. The apparatus as claimed in claim 11 wherein said measuring means comprises a pair of detectors symmetrically disposed on opposite sides of said scanning means at a meridional angle between about 5 degrees and about 60 degrees.

23. The apparatus as claimed in claim 22 wherein said meridional angle is about 30 degrees.

24. The apparatus as claimed in claim 22 wherein said pair of detectors are situated at an azimuthal angle of about 2 to about 10 degrees.

25. The apparatus as claimed in claim 11 further comprising means for trapping the reflection of said beam off the surface of the object.

26. The apparatus as claimed in claim 11 wherein the surface of the object includes a pattern, the apparatus further comprising means for masking the light diffracted by the pattern.

* * * * *